(12) United States Patent
Al Ahmad et al.

(10) Patent No.: US 10,436,772 B2
(45) Date of Patent: Oct. 8, 2019

(54) METHOD AND SYSTEM FOR COUNTING WHITE BLOOD CELLS ELECTRICALLY

(71) Applicant: UNITED ARAB EMIRATES UNIVERSITY, Al Ain (AE)

(72) Inventors: Mahmoud F. Y. Al Ahmad, Al Ain (AE); Shamsa Abdulla Saeed Ali AlHassani, Al Ain (AE); Nouf Ali Salem Mohammed AlNeyadi, Al Ain (AE); Meera Rashed Salem Obaid AlTamimi, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 121 days.

(21) Appl. No.: 15/676,266

(22) Filed: Aug. 14, 2017

(65) Prior Publication Data

US 2017/0370912 A1 Dec. 28, 2017

Related U.S. Application Data

(63) Continuation-in-part of application No. 15/121,958, filed as application No. PCT/IB2014/064042 on Aug. 25, 2014, now Pat. No. 10,078,067.

(51) Int. Cl.
*G01N 33/50* (2006.01)
*G01N 15/06* (2006.01)
(Continued)

(52) U.S. Cl.
CPC ..... *G01N 33/5094* (2013.01); *G01N 15/0656* (2013.01); *G01N 27/226* (2013.01); *G01N 2015/008* (2013.01)

(58) Field of Classification Search
CPC .................................................. G01N 27/48
See application file for complete search history.

(56) References Cited

U.S. PATENT DOCUMENTS 3,678,151 A 7/1972 Horonick et al.
4,058,446 A 11/1977 Zirino et al.
(Continued)

FOREIGN PATENT DOCUMENTS

CA 1259374 9/1989
CN 101625358 A 1/2010
(Continued)

OTHER PUBLICATIONS

Curtis RE, Freedman DM, Ron E, Ries LAG, Hacker DG, Edwards BK, Tucker MA, Fraumeni JF Jr. (eds). New Malignancies Among Cancer Survivors: SEER Cancer Registries, 1973-2000. National Cancer Institute, NIH Publ. No. 05-5302. Bethesda, MD, 2006.
(Continued)

*Primary Examiner* — Christopher E Mahoney
(74) *Attorney, Agent, or Firm* — Perry + Currier, Inc.

(57) ABSTRACT

A system and method for quantifying white blood cells in a blood sample is described. The system includes a sample medium for depositing the same blood. The sample medium is positioned between a first electrode and a second electrode. The system also includes an electrical analyzer for supping pulsing sweeping voltage across the electrodes through the sample medium. The electrical analyzer is also configured for measuring capacitance across the sample medium before and after adding a chemical analyte. The system also includes a general processor in electrical or wireless communication with the electrical analyzer configured for quantifying the white blood cells in the blood sample based on the generated capacitance-voltage profile. The method is described to operate the system and to quantify the white blood cells in a blood sample.

13 Claims, 3 Drawing Sheets

(51) Int. Cl.
G01N 27/22 (2006.01)
G01N 15/00 (2006.01)

(56) References Cited

U.S. PATENT DOCUMENTS

| | | | |
|---|---|---|---|
| 5,476,797 A * | 12/1995 | Matsunaga | G01N 31/22 422/82.01 |
| 6,069,011 A | 5/2000 | Riedel | |
| 6,541,617 B1 | 4/2003 | Bamdad et al. | |
| 6,905,586 B2 * | 6/2005 | Lee | B01L 3/502761 204/450 |
| 8,742,773 B2 | 6/2014 | Elder et al. | |
| 2004/0124084 A1 | 7/2004 | Lee et al. | |
| 2008/0050769 A1 | 2/2008 | Huang et al. | |
| 2008/0262748 A1 | 10/2008 | Ossart et al. | |
| 2014/0024044 A1 * | 1/2014 | Choi | G01N 33/5008 435/7.21 |
| 2014/0323350 A1 | 10/2014 | Nguyen et al. | |
| 2015/0122669 A1 * | 5/2015 | Davis | G01N 33/5438 205/780.5 |
| 2016/0251703 A1 * | 9/2016 | Gilboa-Geffen | C12Q 1/6811 506/1 |
| 2017/0095611 A1 | 4/2017 | Wang et al. | |
| 2017/0160232 A1 | 6/2017 | Al Ahmad | |
| 2017/0173578 A1 | 6/2017 | Crooks et al. | |
| 2017/0350848 A1 | 12/2017 | Wang et al. | |

FOREIGN PATENT DOCUMENTS

| | | |
|---|---|---|
| CN | 101676727 A | 3/2010 |
| CN | 104251810 A | 12/2014 |
| EP | 1688742 A1 | 8/2006 |
| EP | 2908130 A1 | 8/2015 |
| JP | 2002071585 A | 3/2002 |
| JP | 2007271412 A | 10/2007 |
| RU | 2192646 C1 | 11/2002 |
| WO | 02/10754 A2 | 2/2002 |
| WO | WO-2010006253 A1 | 1/2010 |
| WO | WO-2010099618 A1 | 9/2010 |
| WO | WO-2010126897 A1 | 11/2010 |
| WO | WO-2012102584 A2 | 8/2012 |
| WO | WO-2014076506 A1 | 5/2014 |

OTHER PUBLICATIONS

USPTO, Non-Final Rejection, dated Dec. 14, 2017, re U.S. Appl. No. 15/121,958.
EPO, Extended European Search Report, dated Feb. 28. 2018, re European Patent Application No. 14900596.9.
Oer,K. Haematology White Blood Cell Count. Nov. 28, 2011. Retrieved from https://www.youtube.com/watch?v=q6rfJQVSals.
Leeds University. The Histology Guide: White blood cells. 2003. Retrieved from https://www.histology.leeds.ac.uk/blood/blood_wbc.php.
Higuera, Valencia. WBC (White Blood Cell) Count. Mar. 6, 2017. Healthline. Retrieved from: https://www.healthline.com/health/wbc-count.
Hanna, Darrin M., et al. "Detection of vesicular stomatitis virus using a capacitive immunosensor." 2005 IEEE Engineering in Medicine and Biology 27th Annual Conference. IEEE, 2006.
Grigoryev, Y. "Cell Counting with aHemocytometer: Easy as 1, 2, 3". Dec. 12, 2014. BiteSizeBio. Retrieved from: https://bitesizebio.com/13687/cell-counting-with-a-hemocytometer-easy-as-1-2-3/.
International Search Report dated Jan. 14, 2016 for International Patent Application No. PCT/IB2014/064042.
Written Opinion dated Jan. 14, 2015 for International Patent Application No. PCT/IB2014/064042.
Arumugam, M., et al. "Influence of organic waste and inorganic nitrogen source on biomass productivity of Scenedesmus and Chlorococcum sp." Journal homepage: www.IJEE.IEEFoundation.org 2.6 (2011): 1125-1132.
Azmir, Jannatul, et al. "Techniques for extraction of bioactive compounds from plant materials: a review." Journal of Food Engineering 117.4 (2013): 426-436.
Ben-Iwo, Juliet, Vasilije Manovic, and Philip Longhurst. "Biomass resources and biofuels potential for the production of transportation fuels in Nigeria." Renewable and Sustainable Energy Reviews 63 (2016): 172-192.
Bleakley, Stephen, and Maria Hayes. "Algal proteins: extraction, application, and challenges concerning production." Foods 6.5 (2017): 33.
Bligh, E. Graham, and W. Justin Dyer. "A rapid method of total lipid extraction and purification." Canadian journal of biochemistry and physiology 37.8 (1959): 911-917.
Breil, Cassandra, et al. ""Bligh and Dyer" and Folch Methods for Solid-Liquid-Liquid Extraction of Lipids from Microorganisms. Comprehension of Solvatation Mechanisms and towards Substitution with Alternative Solvents."International journal of molecular sciences 18.4 (2017): 708.
Cadenas, Alfredo, and Sara Cabezudo. "Biofuels as sustainable technologies: perspectives for less developed countries."Technological Forecasting and Social Change 58.1-2 (1998): 83-103.
Chen, Chun-Yen, et al. "Microalgae-based carbohydrates for biofuel production." Biochemical Engineering Journal 78 (2013): 1-10.
Chen, Yimin, and Seetharaman Vaidyanathan. "Simultaneous assay of pigments, carbohydrates, proteins and lipids in microalgae." Analytica chimica acta 776 (2013): 31-40.
Converti, Attilio, et al. "Effect of temperature and nitrogen concentration on the growth and lipid content of Nannochloropsis oculata and Chlorella vulgaris for biodiesel production." Chemical Engineering and Processing: Process Intensification 48.6 (2009): 1146-1151.
Pereira Da Costa, Marion, and Carlos Adam Conte-Junior. "Chromatographic methods for the determination of carbohydrates and organic acids in foods of animal origin." Comprehensive Reviews in Food Science and Food Safety 14.5 (2015): 586-600.
Dai, Shuxi, et al. "Structural properties and Raman spectroscopy of lipid Langmuir monolayers at the air-water interface." Colloids and surfaces B: Biointerfaces 42.1 (2005): 21-28.
Erickson, Brent, and Paul Winters. "Perspective on opportunities in industrial biotechnology in renewable chemicals." Biotechnology journal 7.2 (2012): 176-185.
Fakhry, Eman M., and Dahlia M. El Maghraby. "Lipid accumulation in response to nitrogen limitation and variation of temperature in Nannochloropsis salina." Botanical studies 56.1 (2015): 6.
Fu, Chun-Chong, et al. "Hydrolysis of microalgae cell walls for production of reducing sugar and lipid extraction." Bioresource Technology 101.22 (2010): 8750-8754.
Gonzalez Lopez, Cynthia Victoria, et al. "Protein measurements of microalgal and cyanobacterial biomass." Bioresource Technology 101.19 (2010): 7587-7591.
Govender, Trisha, et al. "BODIPY staining, an alternative to the Nile Red fluorescence method for the evaluation of intracellular lipids in microalgae." Bioresource technology 114 (2012): 507-511.
Grosso, Clara, et al. "Alternative and efficient extraction methods for marine-derived compounds." Marine Drugs 13.5 (2015): 3182-3230.
Ruangsomboon, Suneerat, Monthon Ganmanee, and Sakchai Choochote. "Effects of different nitrogen, phosphorus, and iron concentrations and salinity on lipid production in newly isolated strain of the tropical green microalga, Scenedesmus dimorphus KMITL." Journal of applied phycology 25.3 (2013): 867-874.
Hannon, Michael, et al. "Biofuels from algae: challenges and potential." Biofuels 1:5 (2010): 763-784.
Jena, Jayashree, et al. "Microalgae of Odisha coast as a potential source for biodiesel production." World Environment 2.1 (2012): 11-16.
Juneja, Ankita, Ruben Ceballos, and Ganti Murthy. "Effects of environmental factors and nutrient availability on the biochemical composition of algae for biofuels production: a review." Energies 6.9 (2013): 4607-4638.

(56) References Cited

OTHER PUBLICATIONS

Kim, Garam, Ghulam Mujtaba, and Kisay Lee. "Effects of nitrogen sources on cell growth and biochemical composition of marine chlorophyte *Tetraselmis* sp. for lipid production." Algae 31.3 (2016): 257-266.
Krienitz, Lothar, and Manfred Wirth. "The high content of polyunsaturated fatty acids in Nannochloropsis limnetica (Eustigmatophyceae) and its implication for food web interactions, freshwater aquaculture and biotechnology." Limnologica—Ecology and Management of Inland Waters 36.3 (2006): 204-210.
Ranjith Kumar, Ramanathan, Polur Hanumantha Rao, and Muthu Arumugam. "Lipid extraction methods from microalgae: a comprehensive review." Frontiers in Energy Research 2 (2015): 61.
Layne, Ennis. "[73] Spectrophotometric and turbidimetric methods for measuring proteins." (1957): 447-454.
Liu, Zhi-Yuan, Guang-Ce Wang, and Bai-Cheng Zhou. "Effect of iron on growth and lipid accumulation in Chlorella vulgaris." Bioresource technology 99.11 (2008): 4717-4722.
Lohman, Egan J., et al. "An efficient and scalable extraction and quantification method for algal derived biofuel." Journal of microbiological methods 94.3 (2013): 235-244.
Ma, Xiao-Nian, et al. "Lipid production from Nannochloropsis." Marine drugs 14.4 (2016): 61.
Maehre, Hanne K., et al. "Protein Determination—Method Matters." Foods 7.1 (2018): 5.
Mata, Teresa M., Antonio A. Martins, and Nidia S. Caetano. "Microalgae for biodiesel production and other applications: a review." Renewable and sustainable energy reviews 14.1 (2010): 217-232.
Meriluoto, J. "Chromatography of microcystins." Analytica Chimica Acta 352.1-3 (1997): 277-298.
Minhas, Amritpreet K., et al. "A review on the assessment of stress conditions for simultaneous production of microalgal lipids and carotenoids." Frontiers in microbiology 7 (2016): 546.
Oer, K., Course: Pharmacological Lab procedures: Haematology White Blood Cell Count, Nov. 28, 2011, Retrieved from the Internet: https://www.youtube.com/watch?v=q6rfJQVSals.
ISA/AU, International Search Report, dated Jan. 14, 2015, re PCT International Patent Application No. PCT/IB2014/064042.
ISA/AU, Written Opinion, dated Jan. 14, 2015, re PCT International Patent Application No. PCT/IB2014/064042.
ISA/AT, International Search Report, dated Aug. 13, 2015, re PCT International Patent Application No. PCT/IB2015/053861.
ISA/AT, Written Opinion, dated Aug. 13, 2015, re PCT International Patent Application No. PCT/IB2015/053861.
Rajvanshi, Shalini, and Mahendra Pal Sharma. "Micro algae: a potential source of biodiesel." Journal of Sustainable Bioenergy Systems 2.3 (2012): 49.
Sakthivel, Ramasamy. "Microalgae lipid research, past, present: a critical review for biodiesel production, in the future." Journal of Experimental Sciences (2011).
Show, Pau, et al. "A holistic approach to managing microalgae for biofuel applications." International journal of molecular sciences 18.1 (2017): 215.
Simionato, Diana, et al. "Response of Nannochloropsis gaditana to nitrogen starvation includes a de novo biosynthesis of triacylglycerols, a decrease of chloroplast galactolipids and a reorganization of the photosynthetic apparatus." Eukaryotic cell (2013): EC-00363.
Tamburic, Bojan, et al. "The effect of diel temperature and light cycles on the growth of Nannochloropsis oculata in a photobioreactor matrix." PloS one 9.1 (2014): e86047.
Trzcinska, Magdalena, et al. "Genetic and morphological characteristics of two ecotypes of *Eustigmatos calaminaris* sp. nov. (Eustigmatophyceae) inhabiting Zn-and Pb-loaded calamine mine spoils." Fottea 14 (2014): 1-13.
Vrsanska, Martina, and Kumbar Vojtech. "A comparison of Biuret, Lowry and Bradford methods for measuring the egg's proteins." Mendel Net (2015): 394-398.
Wan, Chun, Feng-Wu Bai, and Xin-Qing Zhao. "Effects of nitrogen concentration and media replacement on cell growth and lipid production of oleaginous marine microalga *Nannochloropsis oceanica* DUT01." Biochemical engineering journal 78 (2013): 32-38.
Wells, Mark L., et al. "Algae as nutritional and functional food sources: revisiting our understanding." Journal of applied phycology 29.2 (2017): 949-982.
Wen, Zhiyou, and Michael Ben Johnson. "Microalgae as a feedstock for biofuel production." Virginia Tech Publication 442-886. (2009).
Yang, Xiaohan, et al. "Innovative biological solutions to challenges in sustainable biofuels production." Biofuel Production—Recent Developments and Prospects. InTech, 2011.
Yen, Hong-Wei, et al. "Microalgae-based biorefinery—from biofuels to natural products." Bioresource technology 135 (2013): 166-174.
Yu, Wei-Luen, et al. "Modifications of the metabolic pathways of lipid and triacylglycerol production in microalgae." Microbial cell factories 10.1 (2011): 91.
Zhang, Yun-Ming, et al. "Nitrogen starvation induced oxidative stress in an oil-producing green alga *Chlorella sorokiniana* C3." PloS one 8.7 (2013): e69225.
Zhu, Shunni, et al. "Characterization of lipid and fatty acids composition of Chlorella zofingiensis in response to nitrogen starvation." Journal of bioscience and bioengineering 120.2 (2015): 205-209.
European Patent Office, European Search Report (EPO Form 1507N), dated Mar. 18, 2019 (7 pages).
Fricke H., (1953), 'Relation of the Permittivity of Biological Cell Suspensions to Fractional Cell Volume,' Nature, 172(4381):731-2.
Vykoukal DM et al., (2009), 'Dielectric Characterization of Complete Mononuclear and Polymorphonuclear Blood Cell Subpopulations for Label-Free Discrimination,' Integr Biol (Camb), 1(7):477-84.

\* cited by examiner

| | Shape | WBC's numbers | Size (diameter) Before Disease |
|---|---|---|---|
| Neutrophils | | 2000-7000 | 12-14 μm |
| Lymphocytes | | 1000-3000 | 10-14 μm |
| Monocytes | | 200-1000 | can be up to 20μm |
| Eosinophils | | 20-500 | 12 - 17 μm |
| Basophils | | 20-1000 | 14-16 μm |

FIG. 3
(Prior art)

| Leukemia Types | WBC's Numbers |
|---|---|
| Chronic Lymphocytic Leukemia (CLL) | B-cell: greater than 4000 cells per microliter (μl) of blood, but can be much higher |
| Acute myeloid leukemia (AML) | Normal white blood (not enough red blood and plast) |
| Chronic myeloid leukemia (CML) | Greater than 4000 cells with many early (immature) cells |
| Acute lymphocytic leukemia (ALL) | People with a lower WBC count (less than 30,000 for B-cell ALL and less than 100,000 for T-cell ALL |

FIG. 4
(Prior art)

METHOD AND SYSTEM FOR COUNTING WHITE BLOOD CELLS ELECTRICALLY

CROSS-REFERENCE AND RELATED APPLICATION

This application is a continuation-in-part from application Ser. No. 15/121,958, which is a national Stage of International Application No. PCT/IB2014/064042 filed on 25 Aug. 2014, the entirety of which is incorporated herein.

TECHNICAL FIELD

This invention relates generally to a method and a system for determining cell characteristics and more specifically, to a method for determining electrically white blood cells count and a system configured to establish same.

BACKGROUND

One of the most universally used medical diagnostic lab procedures is the analysis of blood or a patient and identifying the red blood cell count and the white blood cell count in order to determine certain characteristics of such blood. This in turn enables medical practitioners to gain an insight into the patient's health in general and to potentially determine any unwanted intrusions into the patient's body, which could allow for diagnosing the patient.

In recent years, several sensing modalities for detecting and quantifying of biological and chemical analytes in general have been proposed. One of the conventional techniques used for detecting biological analytes in general and blood cells specifically is based on fluorescence exhibited by many analytes of interest generally and blood cells specifically. According to this technique, visible or detectable markers are attached to the blood cells in a blood sample. This method is known as staining. The markers are chosen based on their properties to attach to certain types of biological analytes in the cell but not others. This process is passive and does not change the properties of the analyte of interest but rather change the way it is detected. A complex optical assembly including high intensity optical sources, optical filters and lenses, is then used to detect frequency range of emission, which serve to characterize the analyte of interest.

In cases where the analyte is blood, once the blood sample is stained, manual detection is usually done under a microscope where stained blood cells of interest are counted. The blood count then allows the practitioner to make his or her diagnosis based on the results obtained.

Although such techniques provide good selectivity and sensitivity, the fluorescence-based sensing devices are inherently cumbersome, time consuming, expensive and accordingly, not suitable for many applications such as point-of-care diagnostics.

There is a desire in the field to achieve reliable, time efficient, and cost-effective techniques for identification and quantification of biological and chemical analytes.

SUMMARY OF THE INVENTION

The current disclosure has several aspects. In one aspect of the invention, a method is described for quantifying white blood cells in a blood sample, the method comprising the steps of: depositing the blood sample to a sample medium. The sample medium is positioned between a first electrode and a second electrode. The method also includes providing a pulsating sweep voltage across the first electrode and the second electrode such that a potential gradient is formed across the sample medium. The method further includes depositing a chemical analyte to the blood sample on the same medium. The chemical analyte is for exclusively combining with the white blood cells of the blood sample and for changing the capacitance of the blood sample. The method additionally includes determining a capacitance-voltage profile of the blood sample, before and after depositing the chemical analyte and quantifying the white blood cells in the blood sample based on the determined capacitance-voltage profile.

In a related embodiment, the step of quantifying the white blood cells in the blood sample comprises determining the difference between the capacitance-voltage profile of the blood sample before and after depositing the chemical analyte.

In a related embodiment, the step of determining the capacitance-voltage profile of the blood sample before and after depositing the chemical analyte comprises measuring the capacitance at multiple position on the sample medium and averaging the capacitance measured for a voltage value from the pulsating sweeping voltage.

In a related embodiment, the method further comprises comparing the quantified white blood cells in the blood sample against a look-up table comprising values of known cell counts for known white blood cell types and determining a presence of an abnormality in the blood sample based on the comparison.

In a related embodiment, quantifying the white blood cells in the blood sample is established by the ratio of a total Debye volume of the blood sample; over a volume of a single white blood cell multiplied by the ratio between an extracted Debye length of the blood sample and an extracted Debye length of the sample medium.

In another aspect of the invention, a system for quantifying white blood cells in a blood sample is described. the system comprises a sample medium for holding the blood sample, the sample medium being positioned between a first electrode and a second electrode. The system also includes an electrical analyzer electrically coupled to the first electrode and the second electrode, the electrical analyzer supplying pulsating sweeping voltage across the first electrode and the second electrode such that potential gradient is formed across the sample medium. The electrical analyzer is further configured for measuring capacitance across the sample medium for a given value of pulsating sweeping voltage before and after depositing a chemical analyte to the blood sample to generate a capacitance-voltage profile. The chemical analyte is for exclusively combining with the white blood cells of the blood sample and for changing the capacitance of the blood sample. The system further including a general processor in communication with the electrical analyzer, the general processor configured for quantifying the white blood cells in the blood sample based on the generated capacitance-voltage profile.

In a related embodiment, the first electrode is a moveable electrode. In related embodiment, the second electrode is a fixed electrode resting on a substrate for supporting the second electrode.

In a related embodiment, movement of the moveable electrode is controlled by a controller, where the controller is in wired or wireless communication with the general processor.

In a related embodiment, the moveable electrode has a surface areal less than a surface area of the second electrode or the sample medium.

In a related embodiment, the general processor controls movement of the controller for moving the first electrode to different positions relative to the sample medium, wherein capacitance is measured for each of the different positions.

In a different embodiment, the first electrode comprises an array of electrode arranged to cover different positions of the sample medium and for measuring capacitance across the sample medium for each of the different positions.

In a related embodiment, the general processor determines the quantification of the white blood cells in the blood sample by establishing the ratio of a total Debye volume of the blood sample; over a volume of a single white blood cell multiplied by the ratio between an extracted Debye length of the blood sample and an extracted Debye length of the sample medium.

Other aspects of the invention will be apparent as will be shown in the detailed description of the invention.

BRIEF DESCRIPTION OF THE DRAWINGS

The accompanying drawings illustrate non-limiting example embodiments of the present disclosure.

FIG. 3 shows an example of a look-up table indicating normal WBC counts and sizes for different known WBC types.

FIG. 4 shows an example of a look-up table indicating a correlation between known diseases and WBC.

DETAILED DESCRIPTION

Throughout the following description specific details are set forth in order to provide a more thorough understanding to persons skilled in the art. However, well known elements may not have been shown or described in detail to avoid unnecessarily obscuring the disclosure. The following description of examples of the technology is not intended to be exhaustive or to limit the system to the precise forms of any example embodiment. Accordingly, the description and drawings are to be regarded in an illustrative, rather than a restrictive, sense.

The current disclosure relies on a basic concept of utilizing specific highly selective types of chemicals that have the properties to interact with only the specific type of blood cells of interest. Once such chemicals interact with the cells of interest, such interaction has the effect of changing intrinsic qualities of the cells such as their electrical characteristics. When the blood cells of interest are white blood cells, the technique described in this disclosure allows for electrically obtaining the white blood cell count in the blood sample without the need for traditional visual detection techniques. Calculated white blood cell count based on electrical measurements allows for easy and cost-efficient technique to obtain information that allows medical practitioners to diagnose patients quickly without jeopardizing accuracy.

The use of electrical characteristics for the identification and quantification of biological analytes have been disclosed in U.S. patent application Ser. No. 15/121,958 which content is entirely incorporated herein by reference. In this current disclosure the inventors focus on a related technique for the quantification of white blood cells in a blood sample. However, it is to be understood that the same or similar techniques may be used for quantification of other cells and biological or none biological entities in a biological sample.

White blood cells (WBCs), also called leukocytes, are an important part of the immune system. There are five types of WBCs. These are divided into two main classes Granulocytes (includes Neutrophils, Eosinophils and Basophils) and Agranulocytes (includes Lymphocytes and Monocytes). It is easy to confuse the different leucocytes in blood smears. To identify them, one needs to look for the shape of the nucleus, and compare their size, relative to that of a red blood cell. A low or high WBC count can point to a blood disorder or other medical condition. Leukocytosis is the medical term used to describe a high WBC count. This can be triggered by: anemia, tumors in the bone marrow, inflammatory conditions, such as arthritis and bowel disease, stress, exercise, tissue damage, pregnancy, allergies, asthma and leukemia.

Figure 1:
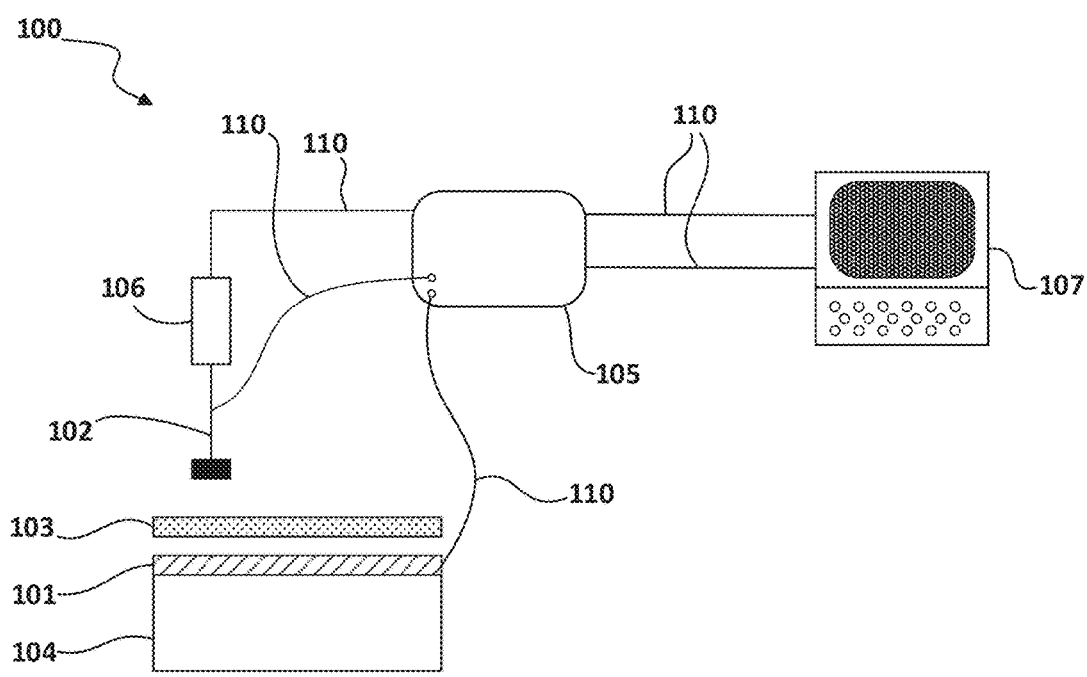
FIG. 1 shows a schematic view of a system for counting white blood cells electrically according to an exemplary embodiment of the present disclosure.

Referring to FIG. 1, a schematic view of system 100 is described for quantification of WBCs in a blood sample in accordance with an exemplary embodiment of the present invention. System 100 comprises a fixed electrode 101 and a moveable electrode 102 to measure capacitance at different locations of a strip 103 positioned between the electrodes. The fixed electrode is deposited on a substrate 104 for supporting the fixed electrode 103. An electrical analyzer 105 is electrically connected to both fixed electrode 103 and moveable electrode 102 via electrical connections 110 to establish and control a potential difference between the two electrodes. The Electrical analyzer 105 is configured to provide a pulsating sweeping voltage to the two electrodes. Capacitance is measured across the fixed and moveable electrodes under the pulsating sweep voltage applied across the electrodes to generate capacitance-voltage profile of the blood sample, which can be used to quantify WBCs in the blood sample, as well be described in detail in a later section of this disclosure.

In the example provided in FIG. 1, moveable electrode 102 is moved and is positions at different locations over the strip 103 and capacitance measurements are obtained for the strip 103 for each of the locations the moveable electrode is moved to. The movement and positioning of the movable electrode 102 is controlled by a control unit 106. The controller 106 may be powered by its own power supply (not shown) or may be powered by voltage supplied from the electrical analyzer 105.

The control unit 106 as well as the voltage pulsating frequency are controlled by a general processor 107 and are connected to it by means of electrical connections 110. In some embodiments, the connection between the controller 106 and the general processor 107 may be wirelessly. In some embodiments, the control unit 106 may be controlled independently from the voltage pulsating frequency. Values of capacitance measured are stored on a memory storage device (not shown) that may be internal or external to the general processor 107.

By having a moveable electrode 102 in system 100, the system allows for collecting multiple capacitance measurements for the same or different pulsating voltage at different locations of the strip 103. This provides accuracy of capacitance measurements using averaging techniques known in the art. In other embodiments (not shown), the moveable electrode 102 may be replaced with an array of electrodes located at prearranged or random locations relating the strip 103. In other embodiments, the arrangement of the electrodes in the electrode array may be configured in accordance with the user's input, which may be programmed into the general processor 107 in accordance with the type and duration of the tests to be conducted.

It should be noted that various electrical properties of the blood sample as measured using system 100 represent the cumulative effect of the electrical properties of the blood and a medium carrying the blood, which is described in FIG. 1 to be strip 103. As will be appreciated, to determine the electrical properties attributable to the WBCs present in the blood sample, it is imperative to take into account the electrical properties of the medium 103 as well as the electrical properties of any chemicals introduced into the strip 103 during operation of system 100.

The current disclosure describes a technique in which WBC count may be achieved only by obtaining a series of electrical measurements such as capacitance measurements of a blood sample using the system described in FIG. 1. As described above, in order to distinguish WBCs in the blood sample that is deposited on a testing strip from other cells such as the red blood cells, a chemical with special characteristics is added to the strip. The function of such chemical is to change the electrical characteristics of only the WBCs without affecting the electrical characteristics of the other elements in the blood sample. Any known chemical known in the art with such characteristics may be used.

By changing the electrical characteristics of the WBCs in the blood sample, it is then understood that capacitance of the blood sample is changed when measured before and after the insertion of the chemical. It is assumed in this technique that capacitance of the chemical, the blood and the strip are additive. The change in capacitance depends on the number of cells inside the blood sample, the chemical added, electrical characteristics of the strip, and the blood content. In designating C1 as the capacitance of the strip by itself, C2 as the capacitance of the strip with the chemical on it, C3 as the capacitance of the strip with the blood sample on it, and C4 as the capacitance of the strip with both the blood and chemical on it, the following mathematical model can be presented:

$$C_2 = C_1 + C_c \quad (1)$$

$$C_3 = C_1 + C_b \quad (2)$$

$$C_4 = C_1 + C_c + C_b^* \quad (3)$$

$C_1$ is a constant value that can be deembedded from other capacitance values. For a single type of chemical, $C_2$ also has a constant value and depend on the added chemical properties. This value also could be deembedded. It is worth noting that the effective capacitance $C_2$ is a parallel combination between the capacitance of the strip $C_1$ and the capacitance of the chemical by itself $C_c$. This is seen in Equation (1) above.

$C_3$ is a variable capacitance, which is based on the blood content. As described in equation (2) above, $C_3$ is expressed as the sum of the constant capacitance value of the strip $C_1$ and the varied capacitance of the blood sample $C_b$. The variance of capacitance for $C_b$ depends mostly on multiple variables including but not limited to the health of the subject from which the blood was taken, the type of food consumed by the person, the age of the person as well as the emotional state of the person among other factors. It is assumed that the capacitance of the blood is independent from that of the strip and is not varied because of the position of the blood on the strip.

$C_4$ in equation (3) above describes the capacitance of the strip, blood and chemical, where it is assumed that the capacitance is parallel and therefore additive. However, it is noted that since the chemical is introduced to the blood, the blood's capacitance is varied from that of the capacitance of the blood without the chemical. This is represented in equation (3) by designating the capacitance of the blood after introducing the chemical as $C_b^*$.

The change in capacitance due to the chemical interaction with the blood is expressed as:

$$\Delta C = C_b^* - C_b \quad (4)$$

By manipulating the equations (1) to (4) above, the change in capacitance cab be expressed in terms of electrically measurable quantities, namely by the expression in equation (5) below:

$$\Delta C = C_4 - C_3 - C_2 + C_1 \quad (5)$$

As the chemical used will only interact with WBC to change its electrical characteristics and will not affect other elements in the blood, therefore, the capacitance change described in equation (4) can be used to obtain a capacitance-voltage profile by measuring the change in blood capacitance over a sweep of voltage pulsating value. Subtracting the capacitance value of the blood before and after it is affected by the chemical has the result of allowing the established value to be directly correlated to the WBC count in the blood sample. By collecting the capacitance change measurements over the sweep of voltage pulsating values, the capacitance voltage profile may then be used to determine the WBC count as will be described below.

Figure 2:
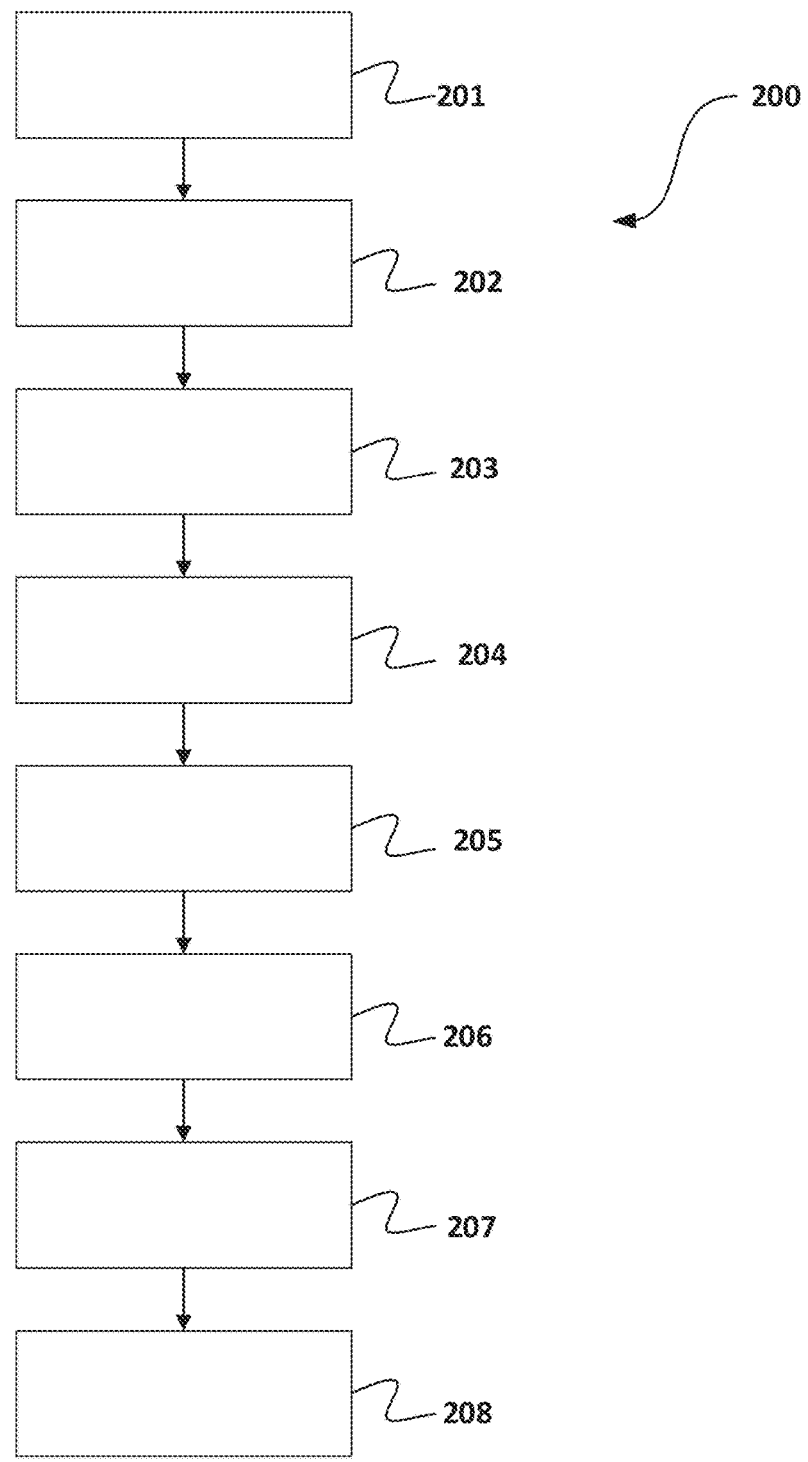
FIG. 2 shows a table flow chart describing the steps of the method used to determine the white blood count in the system shown in FIG. 1.

Referring now to FIG. 2, a flow chart is shown in which a method of operating the system 100 is described for quantification of WBCs in a blood sample in accordance with an exemplary embodiment of the present disclosure. In this embodiment, the system 100 is operated in accordance with a method 200 to quantify WBC's in a blood sample. In a preliminary step, the strip 103 is placed between the fixed electrode 101 and either the movable electrode or a fixed array of electrodes. A voltage is applied across the two electrodes and a capacitance is measured for the strip 103. It is noted that repetition of this step is only required once and that the same capacitance value will act as a constant value so long as the material of the strip is unchanged. In a second step that also does not need to be repeated, a chemical is added to the step and a voltage is applied across the two electrodes. Capacitance for the strip and chemical is measured and is considered a constant for a fixed voltage value so long as the chemical or strip are unchanged.

In Step 203, a blood sample is placed on a second strip and the strip is placed between the electrodes 101 and 102. Voltage is applied from the electrical analyser across the two electrodes 101 and 102 and capacitance is measured for the strip and blood on it. In step 204, the chemical is added to the blood on the strip. Voltage is applied from the electrical analyser and capacitance of the strip, blood and chemical is measured. In step 205, a capacitance-voltage profile of the blood sample is determined. In step 206, the WBC count of the blood sample is quantified based on the capacitance-voltage profile determined.

The number of cells of interest such as WBC or in other exemplary embodiments, red blood cells, present in the medium or sample blood can be quantified by directly linking to the Debye length. Debye length represents an electrical parameter that can be extracted from capacitance-voltage measurements. The basic premise of the technique described in the current disclosure is to consider the buffer control media as a homogenous media along with the other blood contents exempt the white/or red cells and the cells suspended as impurities. Mathematically, the count of the cells is estimated by calculating the impurities inside a defined volume by observing the change in electrical parameters. From the capacitance-voltage measurements, the doping concentration (N) and the Debye Length ($L_D$), can then be computed as follows:

$$N = \left| \left( 0.5 q \varepsilon A^2 \frac{d(c^{-2})}{dV} \right)^{-1} \right| \tag{6}$$

$$L_D = \sqrt{\frac{\varepsilon KT}{q^2 N}} \tag{7}$$

Where: A is the capacitor overlapping area; E is the dielectric constant of the mock material. K, T and q are Boltzmann constant, temperature and electron charge, respectively. The count of cells is suggested empirically to be estimated using the following equation:

$$\text{Count} = (L_{sd}/L_{dm})(A_n \times L_{sd})[\text{Ex}_{volume}]^{-1} \tag{8}$$

Where: $L_{sd}$ is the corresponding extracted Debye length for specific suspension (i.e. the sample blood). $L_{dm}$ is the extracted Debye length for buffer control (i.e. the medium without blood) and $\text{Ex}_{volume}$ is the single cell average volume. $A_n$ is a normalized area and is equal to 1 by 1 m². Equation (8) states that empirically, the number of cells presented in a suspension is approximately equal to the ratio of the corresponding total Debye volume ($A_n L_{sd}$) over the volume of single cell multiplied by the ratio ($L_{sd}/L_{dm}$).

Once the WBC count is determined in the blood sample tested, the value is compared in step 207 against values on a look-up table for known WBC types. FIG. 3 shows normal WBC counts for different known WBC types. FIG. 4 shows a look-up table indicating a correlation between known diseases and WBC.

In step 208, a determination of the existence of abnormalities in the blood sample is made based on the comparison. In some embodiments, where the WBC count is determined to be within the normal range, the user is prompted on the screen of the result and this concludes the operation of system 100. In other embodiments, the system may transmit a signal to a health professional or to a health centre for monitoring the results of the test subject.

In other embodiments, where the WBC count is found to be outside the normal range, the user is prompted of the result and a signal containing the results of the test is transmitted to a health professional or to a health centre for monitoring the results of the test subject. The system may also prompt the use to take an appointment with the health professional to review the results transmitted.

The present disclosure provides a sensing system and a sensing method for quantification of WBCs in a blood sample. The techniques described facilitate label free, reliable, rapid, and low-cost quantification. The techniques of the present disclosure advantageously do not require elaborate sample preparation such as labelling using biomarkers, staining, and so on and are able to produce accurate and reliable results based on electrical measurements of a simply extracted blood sample from the subject. The system described in this disclosure may be used to diagnose certain types of cancer based solely on electrical measurements of a simply extracted blood sample from the subject.

Interpretation of Terms

Unless the context clearly requires otherwise, throughout the description and the claims:

- "comprise," "comprising," and the like are to be construed in an inclusive sense, as opposed to an exclusive or exhaustive sense; that is to say, in the sense of "including, but not limited to".
- "connected," "coupled," or any variant thereof, means any connection or coupling, either direct or indirect, between two or more elements; the coupling or connection between the elements can be physical, logical, or a combination thereof.
- "herein," "above," "below," and words of similar import, when used to describe this specification shall refer to this specification as a whole and not to any particular portions of this specification.
- "or," in reference to a list of two or more items, covers all of the following interpretations of the word: any of the items in the list, all of the items in the list, and any combination of the items in the list.
- the singular forms "a", "an" and "the" also include the meaning of any appropriate plural forms.
- "subject" refers to a human or other animal. It is intended that the term encompass patients, such as vocally-impaired patients, as well as inpatients or outpatients with which the present invention is used as a diagnostic or monitoring device. It is also intended that the present invention be used with healthy subjects (i.e., humans and other animals that are not vocally-impaired, nor suffering from disease). Further, it is not intended that the term be limited to any particular type or group of humans or other animals.
- "power source" and "power supply" refer to any source of electrical power in a form that is suitable for operating electronic circuits.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", "upper", "lower" and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Where a component (e.g. a circuit, module, assembly, device, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of device and method have been described herein for purposes of illustration. These are only examples. The technology provided herein can be applied to device and method other than the examples described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions and sub-combinations as may reasonably be inferred. The scope of the claims should not be limited by the preferred embodiments set forth in the examples, but should be given the broadest interpretation consistent with the description as a whole.

What is claimed is:

1. A method for quantifying white blood cells in a blood sample, the method comprising the steps of:
   depositing the blood sample to a sample medium, the sample medium being positioned between a first electrode and a second electrode;
   providing a pulsating sweep voltage across the first electrode and the second electrode such that a potential gradient is formed across the sample medium;
   depositing a chemical analyte to the blood sample on the same medium, the chemical analyte for exclusively combining with the white blood cells of the blood sample and for changing the capacitance of the blood sample;
   determining capacitance-voltage profiles of the blood sample, before and after depositing the chemical analyte;
   quantifying the white blood cells in the blood sample based on the determined capacitance-voltage profiles.

2. The method of claim 1, wherein quantifying the white blood cells in the blood sample comprises determining the difference between the capacitance-voltage profiles of the blood sample before and after depositing the chemical analyte.

3. The method of claim 1, wherein determining the capacitance-voltage profiles of blood sample before and after depositing the chemical analyte comprises measuring the capacitance at multiple locations on the sample medium and averaging the capacitance measured for a voltage value from the pulsating sweeping voltage.

4. The method of claim 1, the method further comprising comparing the quantified white blood cells in the blood sample against a look-up table comprising values of known cell counts for known white blood cell types; and determining a presence of an abnormality in the blood sample based on the comparison.

5. The method of claim 1, wherein quantifying the white blood cells in the blood sample is established by the ratio of a total Debye volume of the blood sample; over a volume of a single white blood cell multiplied by the ratio between an extracted Debye length of the blood sample and an extracted Debye length of the medium.

6. A system for quantifying white blood cells in a blood sample, the system comprising:
   a sample medium for holding the blood sample, the sample medium being positioned between a first electrode and a second electrode;
   an electrical analyzer electrically coupled to the first electrode and the second electrode, the electrical analyzer supplying pulsating sweeping voltage across the first electrode and the second electrode such that potential gradient is formed across the sample medium, the electrical analyzer further configured for measuring capacitance across the sample medium for a given value of pulsating sweeping voltage before and after depositing a chemical analyte to the blood sample to generate capacitance-voltage profiles;
   a general processor in communication with the electrical analyzer, the general processor configured for quantifying the white blood cells in the blood sample based on the generated capacitance-voltage profiles.

7. The system of claim 6, wherein the first electrode is a moveable electrode.

8. The system of claim 7, wherein the second electrode is a fixed electrode resting on a substrate for supporting the second electrode.

9. The system of claim 7, wherein movement of the moveable electrode is controlled by a controller, the controller in wired or wireless communication with the general processor.

10. The system of claim 9, wherein the moveable electrode has surface areal less than a surface area of the second electrode or the sample medium.

11. The system of claim 10, wherein the general processor controls movement of the controller for moving the first electrode to different positions relative to the sample medium, wherein capacitance is measured for each of the different positions.

12. The system of claim 6, wherein the first electrode comprises an array of electrode arranged to cover different positions of the sample medium and for measuring capacitance across the sample medium for each of the different positions.

13. The system of claim 6, wherein the general processor determines the quantification of white blood cells in the blood sample by establishing the ratio of a total Debye volume of the blood sample; over a volume of a single white blood cell multiplied by the ratio between an extracted Debye length of the blood sample and an extracted Debye length of the medium.

* * * * *